United States Patent
Lee et al.

(10) Patent No.: US 7,589,457 B2
(45) Date of Patent: Sep. 15, 2009

(54) NONDESTRUCTIVE RELIABILITY MONITORING METHOD FOR ADHESIVELY BONDED STRUCTURES WHOSE SENSITIVITY IS IMPROVED BY USING PIEZOELECTRIC OR CONDUCTIVE MATERIALS

(75) Inventors: Dai-Gil Lee, Daejeon (KR); Hui-Yun Hwang, Daejeon (KR); Woo-Seok Chin, Daejeon (KR); Seung-Min Lee, Daejeon (KR); Byung-Chul Kim, Busan (KR); Jae-Wook Kwon, Seoul (KR); Soon-Ho Yoon, Incheon (KR)

(73) Assignee: Korea Advanced Institute of Science and Technology (KR)

( * ) Notice: Subject to any disclaimer, the term of this patent is extended or adjusted under 35 U.S.C. 154(b) by 242 days.

(21) Appl. No.: 11/752,159

(22) Filed: May 22, 2007

(65) Prior Publication Data

US 2007/0214623 A1    Sep. 20, 2007

Related U.S. Application Data

(63) Continuation-in-part of application No. PCT/KR2005/000543, filed on Feb. 28, 2005.

(30) Foreign Application Priority Data

Nov. 23, 2004   (KR) .................. 10-2004-0096491

(51) Int. Cl.
  *H01L 41/113* (2006.01)
(52) U.S. Cl. ...................................... 310/338
(58) Field of Classification Search .......... 310/338
  See application file for complete search history.

(56) References Cited

U.S. PATENT DOCUMENTS

| 2,544,673 A | 3/1951 | Haber |
| 5,345,293 A | 9/1994 | Baek et al. |
| 6,894,427 B2 * | 5/2005 | Alfini .................. 310/338 |

(Continued)

FOREIGN PATENT DOCUMENTS

DE   197 01 462 A 1   * 7/1998

(Continued)

OTHER PUBLICATIONS

PCT International Search Report dated Aug. 22, 2005 regarding PCT Application No. PCT/KR2005/000543.

(Continued)

*Primary Examiner*—Thomas M Dougherty
(74) *Attorney, Agent, or Firm*—Knobbe Martens Olson & Bear LLP

(57) ABSTRACT

A method is disclosed for testing bonded part integrity of bonded structures with increased sensitivity and in a nondestructive manner. The method includes the steps of: mixing a piezoelectric material or an electrically conductive material with an adhesive agent, curing the adhesive agent in between bonding target objects, electrically connecting the bonding target objects to one another, causing an electric current to flow through the bonding target objects to measure a quantity of electric charges flowing between the bonding target objects, and determining existence of bonding damage between the bonding target objects and the adhesive agent based on the quantity of electric charges and predicting a remaining life span of the bonded structures based on a data indicating a correlation between the quantity of electric charges and a predetermined fatigue life.

22 Claims, 6 Drawing Sheets

U.S. PATENT DOCUMENTS 5,245,293 A    9/1993    Runner

FOREIGN PATENT DOCUMENTS

| | | |
|---|---|---|
| JP | 2001-033415 A | 2/2001 |
| JP | 2002-098626 A | 4/2002 |
| KR | 10-2005-0030696 A | 3/2005 |

OTHER PUBLICATIONS

Kwon, Chin, and Lee, "Reliability Monitoring of Adhesive Joints by Piezoelectricity," Journal of the Korean Society of Mechanical Engineering (2003) vol. 27, No. 8, pp. 1388-1397.

Kwon, Chin, and Lee, "Piezoelectric monitoring of the reliability of the adhesive joints," Journal of Adhesion Science Technology (2003), vol. 17, No. 6, pp. 777-796.

Hwang, Kim, Chin, Kim, and Lee, "Prediction of crack length and crack growth rate of adhesive joints by a piezoelectric method," J. Adhesion Sci. Technol. (2005) vol. 19, No. 12, pp. 1081-1111.

Hwang and Lee, "Diagnosis criterion for damage monitoring of adhesive joints by a piezoelectric method," J. Adhesion Sci. Technol. (2005) vol. 19, No. 12, pp. 1053-1080.

* cited by examiner

NONDESTRUCTIVE RELIABILITY MONITORING METHOD FOR ADHESIVELY BONDED STRUCTURES WHOSE SENSITIVITY IS IMPROVED BY USING PIEZOELECTRIC OR CONDUCTIVE MATERIALS

CROSS-REFERENCE TO RELATED PATENT APPLICATIONS

This application is a continuation-in-part application under 35 U.S.C. § 365(c) of International Application No. PCT/KR2005/000543, filed Feb. 28, 2005 designating the United States. International Application No. PCT/KR2005/000543 was published in English as WO2006/057482 A1 on Jun. 1, 2006. This application further claims the benefit of the earlier filing dates under 35 U.S.C. § 365(b) of Korean Patent Application No. 10-2004-0096491 filed Nov. 23, 2004. This application incorporates herein by reference the International Application No. PCT/KR2005/000543 including the International Publication No. WO2006/057482 A1 and the Korean Patent Application No. 10-2004-0096491 in their entirety.

BACKGROUND

1. Field

The present disclosure relates to a method for nondestructively testing, and more particularly, to a method of testing adhesively bonded structures.

2. Discussion of the Related Technology

Keeping pace with the recent trend toward the use of increasing number of structures fabricated with high strength steels, there have been proposed a variety of methods for inspecting a welding condition and monitoring a fatigue-caused crack with respect to a bonded part of the steel structures. These methods are nondestructive in view of the fact that the monitoring task for a bonded condition should be conducted without destroying the structures. Examples of major testing methods developed thus far includes a radiography, an ultrasonic flaw detecting method, a magnetic powder flaw detecting method, a dye infiltrating method, an eddy current method and so forth.

However, such methods are problematic in terms of the following aspects. Among others, the radiography makes use of a radiation harmful to the human body and therefore may injure not only the health of an operator in the testing process but also the health of a person who comes close to the monitored structures with a residual radiation. Furthermore, the radiography exhibits a reduced testing speed, costs a great deal in conducting the test and has no ability to perform a real time test while the structures are in operation.

The ultrasonic flaw detecting method is said to be safer and more economical than the radiography. But the ultrasonic flaw detecting method makes it difficult to analyze the signals indicative of the ultrasonically detected results and may suffer from a problem in processing the signals due to the presence of noises. Additionally, the ultrasonic flaw detecting method requires a signal reception and analysis process, thus making it impossible to carry out the test on a real time basis.

In case of the magnetic powder flaw detecting method, the material that can be monitored by the same is confined to a conductive one. Further, no accurate test result can be derived because a high voltage current for forming magnetic fields adversely affects a test device. In addition, the magnetic powder flaw detecting method has no ability to carry out the test on a real time basis. Just like the magnetic powder flaw detecting method, the eddy current flaw detecting method is applicable only to a conductive material and has a disadvantage in that the test results are sensitively changed depending on the surface condition of the bonded part.

Also known is an acoustic inspection method that can monitor the condition of an overall structure on a real time basis and can be applicable to a wide range of materials. However, the acoustic inspection method shows different test results depending on the sensitivity of sensors employed and is heavily affected by the shape of a structure, thereby encountering a difficulty in accurately detecting the location of a flaw.

In addition to the above, the exemplary nondestructive test techniques including the radiography, the ultrasonic flaw detecting method, the magnetic powder flaw detecting method, the dye infiltrating method, the eddy current method and the like are restrictively used in detecting an internal defect, a surface flaw and a damage of those steel structures fabricated by welding joints. For this reason, the exemplary test techniques are unsuitable for use with adhesively bonded joints or composite structures made of newly developed materials. Moreover, the exemplary test techniques require the use of costly equipments and lack an ability to predict the remaining life span of a structure because they are dedicated to testing the current structure condition.

In consideration of the drawbacks posed in the exemplary test methods, extensive researches have been made for a technique of testing the load delivery capability and the integrity of adhesively bonded joints on a real time basis. As a result, there have been developed a variety of methods for diagnosing the integrity of a structure on a real time basis. U.S. Pat. No. 5,245,293 discloses a method for real-time testing the bonded part integrity of adhesively bonded structures. In this patent, a bonded condition is detected by allowing an electric current to flow through object members bonded together by an adhesive agent and then measuring the change in resistance or capacitance thereof. However, the technology disclosed is adapted to monitor the bonded condition not by the quantitative values of the resistance or capacitance but by the change in such values. Inasmuch as the capacitance of the bonded part varies sensitively with the ambient temperature, the humidity, the length of conductive lines, the floating capacitance or the like, the technology disclosed has a drawback in that it has no ability to accurately judge the bonded condition.

Korean Patent Application No. 10-2003-0066640 teaches a method for testing the bonded part integrity of adhesively bonded structures through the use of a piezoelectric characteristic of an adhesive. In this technology, use is made of the piezoelectric characteristic that the adhesive agent emits electric charges as it is pressed. Namely, the integrity of the adhesively bonded structures is tested by connecting conductive lines to the objects bonded together and monitoring the quantity of electric charges emitted through the conductive lines.

FIG. 1 is a graph showing the correlation between a density of electric charges and a fatigue life at the time when an adhesive agent receives a specific kind of fatigue load. In FIG. 1, the density of electric charges is obtained by dividing the quantity of electric charges by the bonding area of the objects bonded with an adhesive agent, and the fatigue life represents a value measured by applying the specific kind of fatigue load to the adhesive agent on a cycle-by-cycle basis.

Under a fixed load, the stress acting on an adhesive agent is inversely proportional to the area of a bonded surface and the density of electric charges is proportional to the stress, which means that the density of electric charges is increased in proportion to the decrease of the bonded area. Accordingly, an increase in the density of electric charges means a decrease in the bonded area which in turn represents an increase in the separated area. Thus, if physical properties (a piezoelectric constant, a tensile strength, a compression strength, a sheer strength and the like) are measured for varying kinds of adhesive agents and if the kinds of loads applied (a tensile load, a compression load and a sheer load) are determined, after which the correlation between an electric charge density and a fatigue life is set in advance, it becomes possible to evaluate the integrity and the remaining life of bonded structures by measuring the quantity of the electric charges generated from a bonded part at an arbitrary time. Further, since the quantity of the electric charges is measured over the entire bonded parts, the integrity test can be conducted for the bonded parts as a whole. The correlation between the stress developed in the bonded structures and the electric charge density is disclosed by the inventor of the subject patent application (2003), "Piezoelectric Monitoring of the reliability of adhesive joints", *Journal of Adhesion Science Technology*, Vol. 17, No. 6, pp. 777-796.

A exemplary technique that uses, for the purpose of testing bonded part integrity, an epoxy-based adhesive agent which is one of typical adhesive agents and exhibits an extremely weak piezoelectric characteristic. According to this technique, the epoxy-based adhesive agent, which is disposed between target objects to bond them together, emits electric charges by its piezoelectric characteristic in the event that a pressure is applied thereto. Thus, if the bonded objects are electrically connected to one another, it is possible to measure the quantity of the electric charges flowing therebetween. As shown in Table 1 below, however, the typical epoxy-based adhesive agent has an extremely low piezoelectric constant. Therefore, the epoxy-based adhesive agent has a shortcoming in that a relatively small quantity of electric charges is measured in the process of testing bonded part integrity of bonded structures, thus reducing the test sensitivity. In order to easily detect the relatively small quantity of electric charges, it is unavoidable to employ such a means as an amplifier.

TABLE 1

| Adhesive Agent | Piezoelectric Stress Constant (pC/N) | Piezoelectric Strain Constant ($10^{-3}$ C/m$^2$) |
|---|---|---|
| PZT(Pb(Zn—Ti)O$_3$) | 120 | 18 |
| PVDF | 30 | 16 |
| PVC | 1 | 3 |
| Nylon 11 | 0.3 | 0.5 |
| Rubber | 0.1 | 0.0001~0.001 |
| Epoxy (Rubber Toughened) | 0.029 | 0.027 |
| Epoxy (Without Rubber) | 0.019 | 0.057 |

The foregoing discussion in this section is to provide general background information, and does not constitute an admission of prior art.

SUMMARY

An aspect of the invention provides an apparatus comprising: a first piece comprising a first surface; a second piece comprising a second surface facing the first surface; an adhesive layer interposed between the first and second surfaces, wherein the adhesive layer contacting and integrating the first and second surfaces; wherein the adhesive layer comprises an adhesive material with a piezoelectricity and piezoelectric particles dispersed in the adhesive material, wherein the piezoelectric particles have substantially higher piezoelectricity than the adhesive material.

In the foregoing apparatus, the adhesive layer may be configured to generate electric charges upon application of sufficient force between the first and second pieces. The adhesive material may comprise an epoxy polymer resin. The piezoelectric particles may comprise at least one selected from the group consisting of piezoelectric crystal particles, piezoelectric ceramic particles, piezoelectric polymer particles and piezoelectric semiconductor particles. The piezoelectric particles may comprise at least one selected from the group consisting of PZT(Pb(Zn—Ti)O$_3$, PVDF, PVC, nylon, rubber and quartz. The adhesive material may have a piezoelectric stress constant smaller than about 0.1 pC/N. The piezoelectric particles may have a piezoelectric stress constant greater than about 1 pC/N. The piezoelectric particles may have a piezoelectric stress constant greater than about 30 pC/N. The total volume of the piezoelectric particles may be from about 5% to about 30% of the volume of the adhesive layer. At least part of the piezoelectric particles may have a particle size from about 10 nm to about 10 μm.

Still in the foregoing apparatus, the apparatus may further comprise a first electrode as part of the first piece or as separate and interposed between the first piece and the adhesive layer, a second electrode as part of the second piece or as separate and interposed between the second piece and the adhesive layer, and wherein the adhesive layer may be configured to generate electric charges upon application of sufficient force between the first and second pieces. At least part of the piezoelectric particles may have an elongated shape elongated in a longitudinal direction thereof, wherein the longitudinal direction may be oriented generally perpendicular to the first surface. At least part of the piezoelectric particles may have an elongated shape elongated in a longitudinal direction thereof, wherein the longitudinal direction may be oriented generally parallel to the first surface. At least one of the first and second pieces may receive a substantially constant pressure which applies a force in a direction, wherein the direction may comprise at least one of a first directional component perpendicular to the first surface and a second directional component perpendicular to the first component. The apparatus may comprise an airplane. The apparatus may comprise a ship comprising a tank for containing liquefied gas.

Another aspect of the invention provides a method of testing bonded pieces, comprising: providing the apparatus of claim 1; applying a predetermined amount of pressure onto at least one of the first and second pieces so as to apply a force to the adhesive layer, whereby the adhesive layer generates electric charges in the adhesive layer; detecting a charge density of the electric charges; and processing the charge density.

In the foregoing method, processing the charge density may be to determine the stability of the interconnection of the first and second pieces via the adhesive layer. Processing may comprise comparing the charge density with a reference value. The reference value may comprise a charge density detected from the adhesive layer at a prior time using the same amount of force applied onto at least one of the first and second pieces in the same or substantially the same manner. Processing the current density may be to estimate life expectancy of the interconnection of the first and second pieces via the adhesive layer. Processing the current density may be to determine an existence of damage to the adhesive layer.

An aspect of the present invention to provide a method capable of testing bonded part integrity of adhesively bonded structures with enhanced sensitivity by admixing an adhesive agent with a piezoelectric material or a conductive material and thus improving a piezoelectric characteristic or electric conductivity of the adhesive agent.

Another aspect of the present invention is to provide a method capable of testing bonded part integrity of adhesively bonded structures without resort to a separate signal amplifier by increasing the quantity of electric charges generated when a pressure is applied to an adhesive agent between bonded objects.

According to an aspect of the present invention, use is made of an adhesive agent admixed with a piezoelectric material or a conductive material whose thermal expansion coefficient is relatively small. This provides a beneficial effect in that it is possible to reduce damage of a bonded part which would otherwise be caused by residual stresses. Another beneficial effect is that the piezoelectric material or the conductive material plays a role of a crack propagation inhibitor, thereby prolonging a fatigue life of adhesively bonded structures.

The above and other aspects, features and advantages of the present invention will become apparent from the following description of embodiments given in conjunction with the accompanying drawings.

An aspect of the present invention is directed to a method for testing bonded part integrity of bonded structures with increased sensitivity and in a nondestructive manner, wherein the bonded structures are bonded together with an adhesive agent having a piezoelectric characteristic and wherein a piezoelectric material is admixed with the adhesive agent to enhance the piezoelectric characteristic.

Another aspect of the present invention is directed to a method for testing bonded part integrity of bonded structures with increased sensitivity and in a nondestructive manner, comprising the steps of: mixing a piezoelectric material or an electrically conductive material with an adhesive agent, curing the adhesive agent in between bonding target objects, electrically connecting the bonding target objects to one another, causing an electric current to flow through the bonding target objects to measure a quantity of electric charges flowing between the bonding target objects, and determining existence of bonding damage between the bonding target objects and the adhesive agent based on the quantity of electric charges and predicting a remaining life span of the bonded structures based on a data indicating a correlation between the quantity of electric charges and a predetermined fatigue life.

DETAILED DESCRIPTION OF EMBODIMENTS

Figure 2:
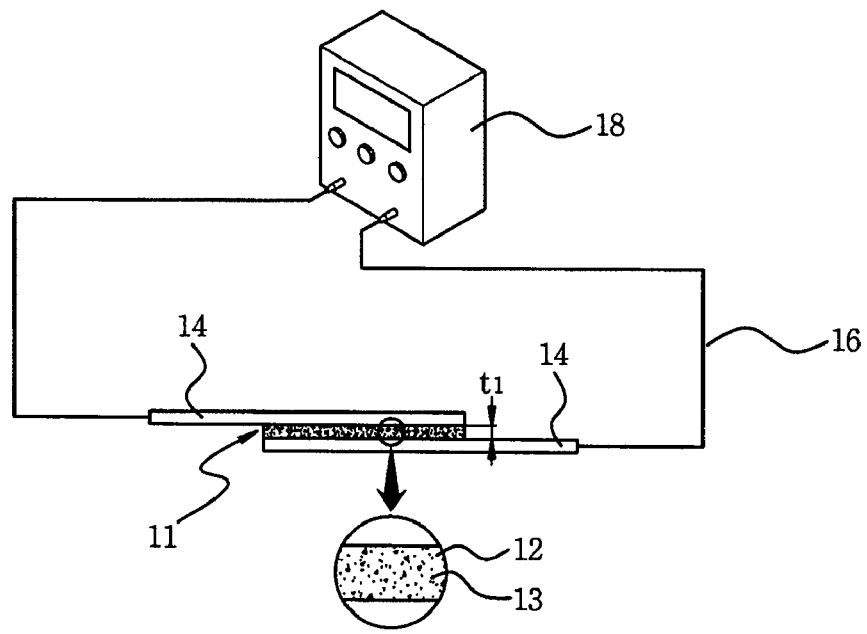
FIG. 2 is a conceptual diagram showing a method for testing bonded structures in accordance with an embodiment of the present invention.

Referring to FIG. 2, there is shown a conceptual diagram of bonded structures and a test method in accordance with an embodiment of the present invention. As shown, an adhesive agent 11 is disposed between two bonding target objects 14.

The adhesive agent 11 is produced by admixing a high molecular resin material 12 having bondability with a piezoelectric material 13. The high molecular resin material 12 may be comprised of, e.g., an epoxy resin having a piezoelectric characteristic and bondability. The piezoelectric material 13 refers to a material that creates a pressure when supplied with an electric current or generates an electric current as a pressure is applied thereto. Such a piezoelectric material 13 is comprised of a material having an increased piezoelectric constant, e.g., a piezoelectric crystal, a piezoelectric ceramics, a piezoelectric polymer, a piezoelectric semiconductor or the like.

The piezoelectric constants of these piezoelectric materials are shown in Table 1 as presented earlier. As can be seen in Table 1, PZT(Pb(Zn—Ti)O$_3$), lead zirconium titanate which is a piezoelectric ceramics, has a piezoelectric stress constant of 120 pC/N and a piezoelectric strain constant of $18 \times 10^{-3}$ C/m$^2$, which piezoelectric constants are greatest among those of the materials shown in Table 1. It can be appreciated that PVDF (polyvinylidene fluoride), PVC (polyvinyl chloride) and nylon 11, all of which are piezoelectric polymer materials, have piezoelectric constants smaller than those of PZT but greater than those of the epoxy resin.

In one embodiment, the piezoelectric stress constant of the piezoelectric material of piezoelectric particles is greater than about 0.1 pC/N. In certain embodiments, the piezoelectric stress constant of the piezoelectric material is about 0.1 pC/N, about 0.2 pC/N, about 0.3 pC/N, about 0.5 pC/N, about 1 pC/N, about 10 pC/N, about 20 pC/N, about 30 pC/N, about 40 pC/N, about 50 pC/N, about 60 pC/N, about 70 pC/N, about 80 pC/N, about 90 pC/N, about 100 pC/N, about 110 pC/N, about 120 pC/N, about 130 pC/N, about 150 pC/N or about 200 pC/N. In some embodiments, the piezoelectric stress constant of the piezoelectric material may be within a range defined by two of the foregoing piezoelectric stress constants.

In the event that the adhesive agent 11 is prepared by admixing the piezoelectric material 13 of greater piezoelectric constants with the epoxy-based high molecular resin material 12 in this manner, the piezoelectric constants of the adhesive agent 11 become greater than the piezoelectric constants before the piezoelectric material 13 is added. Thus, the bonded parts generate a greater quantity of electric charges for the same magnitude of an external force applied thereto, consequently improving the test sensitivity.

Preferably, the piezoelectric material 13 is a powder of the material having a piezoelectric characteristic. This makes it possible to measure the quantity of electric charges evenly over the entire bonding surface. The particle size of the piezoelectric material 13 is preferably in the range of about 10 nm to about 10 μm. In certain embodiments, the particle size is about 10 nm, about 20 nm, about 30 nm, about 50 nm, about 100 nm, about 200 nm, about 300 nm, about 400 nm, about 500 nm, about 600 nm, about 700 nm, about 800 nm, about 900 nm, about 1 μm, about 1.5 μm, about 2 μm, about 2.5 μm, about 3 μm, about 5 μm, about 7 μm, about 10 μm or about 20 μm. In some embodiments, the particles size may be within a range defined by two of the foregoing particle sizes. In an embodiment, no particular restriction is imposed on the particle size as far as it is smaller than the thickness $t_1$ of the adhesive agent 11.

The piezoelectric material 13 may have a variety of shapes, e.g., a spherical shape, an elliptical shape, a plate shape, a hexahedral shape or the like. If the piezoelectric material 13 is of a spherical shape, the piezoelectric characteristic of the piezoelectric material 13 becomes isotropic when a pressure is given thereto. In case where an external pressure is exerted on the bonded structures in a specific direction, however, it is preferred for improvement of the piezoelectric characteristic or the mechanical properties that the piezoelectric material 13 of an elliptical shape, a plate shape or a hexahedral shape is aligned within the adhesive agent 11 in a direction in which the external force is exerted.

Ends of the bonding target objects are connected through conductive wires to an electric charge measuring device 18 that measures the quantity of electric charges flowing between the bonding target objects 14. As a result, the electric charge measuring device 18 can measure the quantity of electric charges flowing through the adhesive agent 11 disposed between the bonding target objects 14.

Figure 3:
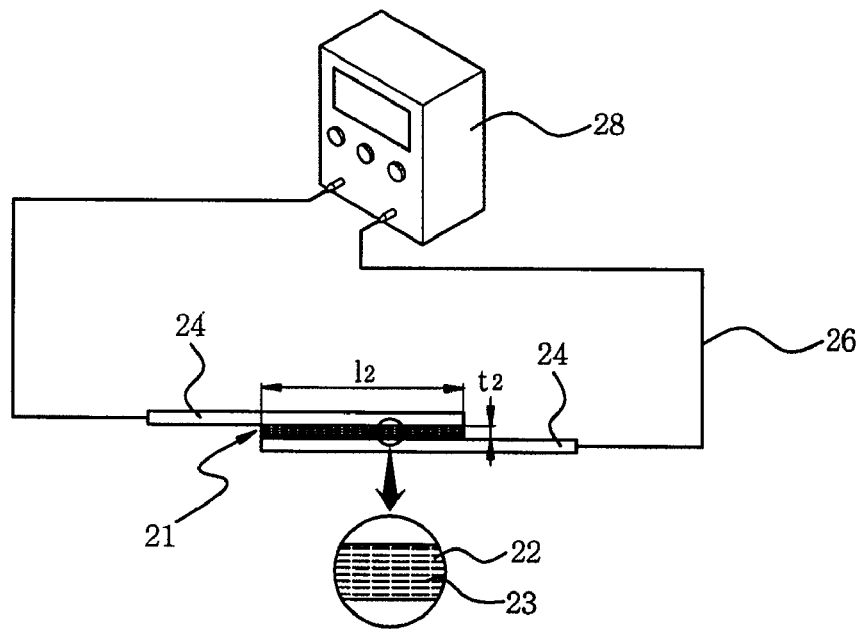
FIG. 3 is a conceptual diagram showing a method for testing bonded structures in accordance with an embodiment of the present invention.

FIG. 3 is a conceptual diagram showing a method for testing bonded structures in accordance with an embodiment of the present invention. As shown in this figure, an adhesive agent 21 is disposed between two bonding target objects 24. The method of the illustrated embodiment is the same as that of the above discussed embodiment except that piezoelectric monofilaments 23 are used as the piezoelectric material 13. Therefore, no detailed description will be given to the same parts or components.

The adhesive agent 21 is produced by mixing an epoxy-based high molecular resin material 22 with the piezoelectric monofilaments 23 of elongated configuration. The high molecular resin material 22 is comprised of a material having an infinitesimal piezoelectric characteristic and a bonding force as in the embodiments set forth above. Since the adhesive agent 21 has a length l2 greater than a thickness t2, most of the piezoelectric monofilaments 23 are oriented in a longitudinal direction of the adhesive agent 21.

Thus, the quantity of electric charges generated by the force acting in the longitudinal direction l2 of the piezoelectric monofilaments 23 is greater than the quantity of electric charges generated by the force exerted in the thickness direction t2 thereof. This means that the quantity of electric charges generated when an external force is exerted in the longitudinal direction of the bonding target objects 24 is greater than the quantity of electric charges generated when a compression force acts between the bonding target objects 24. Further, the mechanical properties of the adhesive agent 21 such as a mechanical strength or the like becomes greater in the longitudinal direction l2 of the piezoelectric monofilaments 23 than in the thickness direction t2 thereof. Accordingly, it is preferred that the piezoelectric monofilaments 23 are used in case of the external force being exerted in the longitudinal direction l2 rather than in the thickness direction t2.

Preferably, the piezoelectric monofilaments 23 are produced to have a length of about 10 μm to about 10 mm and a diameter of about 10 nm to about 10 μm. In certain embodiments, the length is about 10 μm, about 20 μm, about 30 μm, about 50 μm, about 70 μm, about 100 μm, about 200 μm, about 300 μm, about 400 μm, about 500 μm, about 600 μm, about 700 μm, about 800 μm, about 900 μm, about 1 mm, about 1.5 mm, about 2 mm, about 2.5 mm, about 3 mm, about 5 mm, about 7 mm, about 10 mm or about 20 mm. In some embodiments, the length may be within a range defined by two of the foregoing lengths. In certain embodiments, the diameter is about 10 nm, about 20 nm, about 30 nm, about 50 nm, about 100 nm, about 200 nm, about 300 nm, about 400 nm, about 500 nm, about 600 nm, about 700 nm, about 800 nm, about 900 nm, about 1 μm, about 1.5 μm, about 2 μm, about 2.5 μm, about 3 μm, about 5 μm, about 7 μm, about 10 μm or about 20 μm. In some embodiments, the diameter may be within a range defined by two of the foregoing diameters. In an embodiment, no particular restriction is imposed on the length and the diameter as far as the piezoelectric monofilaments 23 have a length smaller than the length l2 of the adhesive agent 21 and a diameter smaller than the thickness t2 of the adhesive agent 21.

Figure 4:
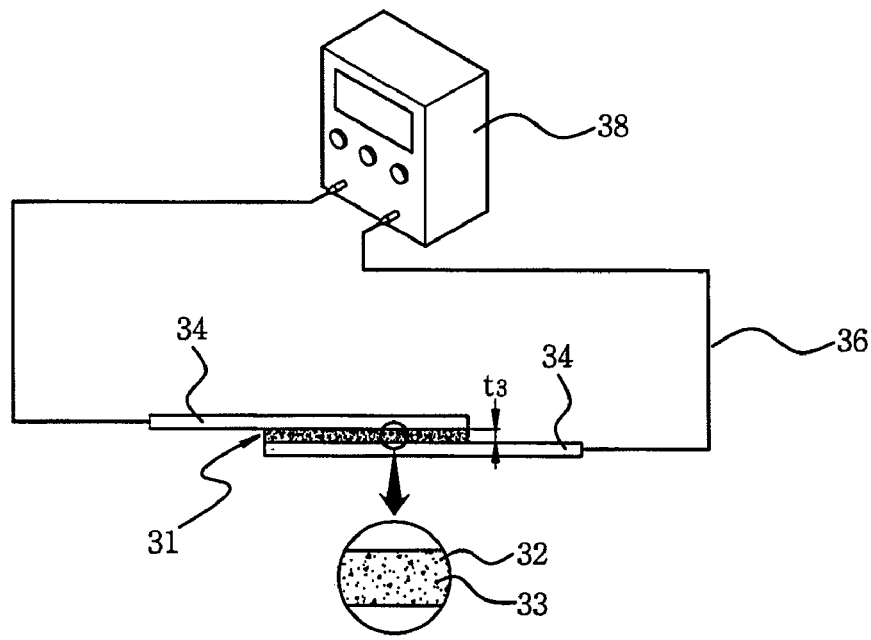
FIG. 4 is a conceptual diagram showing a method for testing bonded structures in accordance with an embodiment of the present invention.

FIG. 4 is a conceptual diagram showing a method for testing bonded structures in accordance with an embodiment of the present invention. As shown in this figure, an adhesive agent 31 is disposed between two bonding target objects 34. The method of the embodiment is the same as that of the embodiment except that an electrically conductive material 33 is used in place of the piezoelectric material 13. Therefore, no detailed description will be given to the same parts or components.

The adhesive agent 31 is produced by mixing a high molecular resin material 32 having bondability with the electrically conductive material 33. The high molecular resin material 32 is comprised of an epoxy resin or like materials having an infinitesimal piezoelectric characteristic and a bonding force as in the embodiments set forth above. The electrically conductive material 33 is comprised of powder particles which are excellent in electric conductivity. Examples of such an electrically conductive material include metals such as copper, silver, iron or the like, carbon, carbon black and so forth. Table 2 shows the electric conductivity of these materials.

TABLE 2

| Kinds of Materials | Electric Conductivity (1/Ωm) |
| --- | --- |
| Aluminum | $35.3 \times 10^6$ |
| Copper | $58.0 \times 10^6$ |
| Gold | $41.0 \times 10^6$ |
| Iron | $10.3 \times 10^6$ |
| Silver | $62.9 \times 10^6$ |
| Epoxy | $10^{-12} \sim 10^{-13}$ |

As can be seen in Table 2, the electrically conductive metals have electric conductivity far greater than that of epoxy. This means that the adhesive agent 31 mixed with the electrically conductive material 33 exhibits far greater electric conductivity than an adhesive agent free from the electrically conductive material. Therefore, the adhesive agent 31 containing the electrically conductive material 33 is capable of efficiently transmitting the electric charges generated around a crack part of the adhesive agent to the bonding target objects 34, consequently enhancing the sensitivity of measuring the quantity of electric charges.

The electrically conductive material 33 is preferable comprised of powder of a material excellent in electric conductivity. This makes it possible to measure the quantity of electric charges without deviation over the entire bonding surface in the process of testing bonded part integrity. Particle size of the electrically conductive material 33 is in the range of several tens nm to several μm. Further, the particle size of the electrically conductive material 33 is so selected to be smaller than the thickness t3 of the adhesive agent 31. This is to ensure that the thickness t3 of the adhesive agent 31 is not restricted by the particle size of the electrically conductive material 33.

As with the piezoelectric material 13 stated earlier in respect of the embodiment, the electrically conductive material 33 may have a variety of shapes, e.g., a spherical shape, an elliptical shape, a plate shape, a hexahedral shape or the like. If the electrically conductive material 33 is of a spherical shape, the electrically conductivity of the electrically conductive material 33 becomes isotropic.

Figure 5:
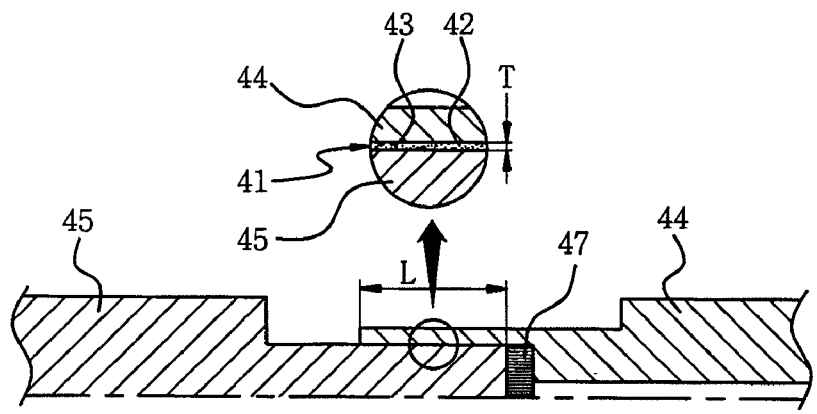
FIG. 5 is a cross-sectional view illustrating a specimen of cylindrical shape for a torsional fatigue test produced in accordance with an embodiment of the present invention.
Figure 6:
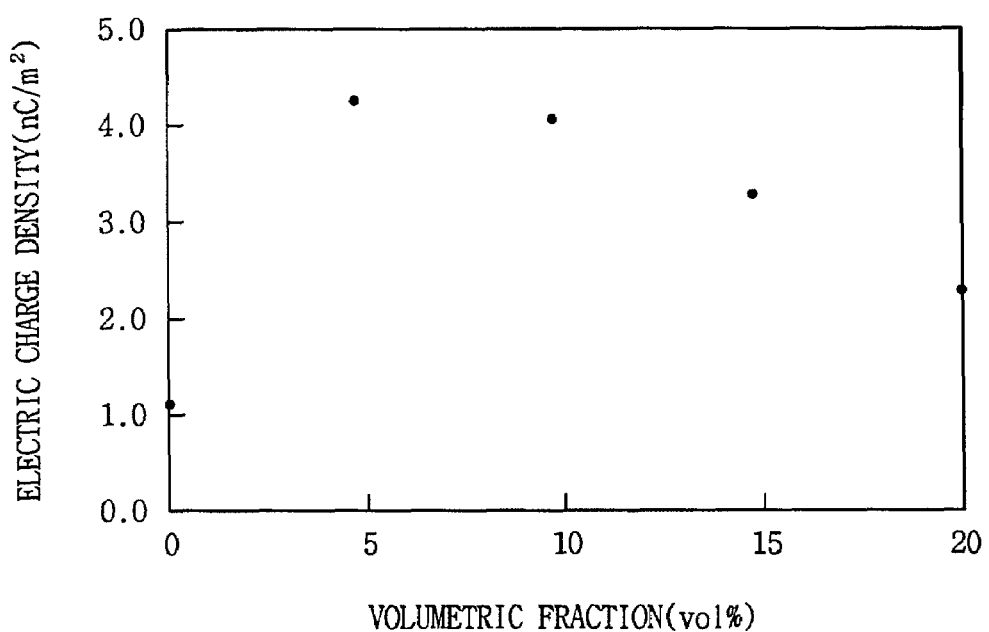
FIG. 6 is a graph representing the correlation between a volumetric fraction of a piezoelectric material within an adhesive agent and an electric charge density at 1,000 cycles measured for the specimen illustrated in FIG. 5.
Figure 7:
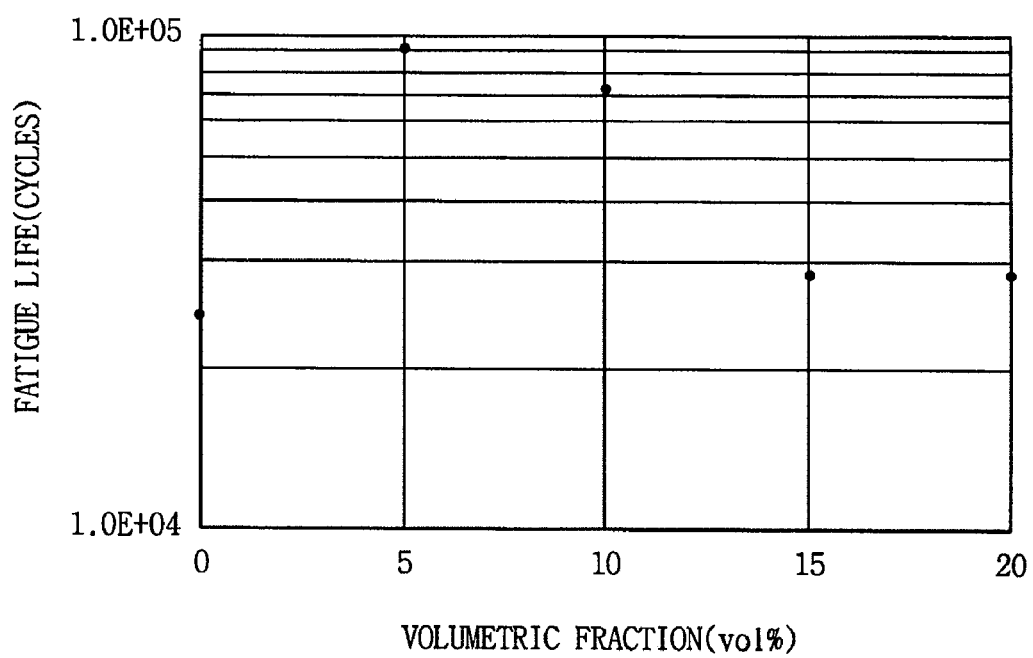
FIG. 7 is a graph representing the correlation between a volumetric fraction of a piezoelectric material within an adhesive agent and a fatigue life measured for the specimen illustrated in FIG. 5.

FIG. 5 is a cross-sectional view illustrating a specimen of cylindrical shape for a torsional fatigue test produced by use of the adhesive agent in accordance with an embodiment of the present invention, FIG. 6 is a graph representing the correlation between a volumetric fraction of a piezoelectric material within an adhesive agent and an electric charge density at 1,000 cycles measured for the specimen illustrated in FIG. 5, and FIG. 7 is a graph representing the correlation between a volumetric fraction of a piezoelectric material within an adhesive agent and a fatigue life measured for the specimen illustrated in FIG. 5.

The adhesive agent 41 is composed of an epoxy-based high molecular resin material 42 and a piezoelectric material 43, both of which are mixed with each other. In the test illustrated in FIG. 5, quartz particles whose average size is 0.8 μm were used as the piezoelectric material 43. An average shear force of 8 MPa was applied in the test.

For the purpose of testing bonded part integrity by applying a torsional force, bonding target objects 44 and 45 are formed in a cylindrical shape and adhesively bonded with each other at predetermined areas. Further, the bonding target objects 44 and 45 are bonded to one another by a tubular single lap joint whose cross-section is of circular shape. These bonding target objects 44 and 45 are comprised of an outer bonding target object 44 and an inner bonding target object 45 bonded to one end surface of the outer bonding target object 44 by a length L. A Teflon spacer 47 is provided between and keeps spaced apart the outer bonding target object 44 and the inner bonding target object 45 at their parts remaining not bonded. This is to obtain a data regarding the quantity of electric charges only for the bonded part of the outer bonding target object 44 and the inner bonding target object 45 which corresponds to the length L.

Referring to FIG. 6, it can be confirmed that the bonding target objects 44 and 45 bonded by the adhesive agent 41 containing quartz particles as the piezoelectric material 43 generate electric charges of greater density than the bonding target objects bonded by the adhesive agent containing no quartz particle. In the case where the volumetric fraction of the piezoelectric material 43 contained in the adhesive agent 41 is 5 vol %, the electric charge density measured was about 4.3 nC/m$^2$. In the event that the volumetric fraction of the piezoelectric material 43 contained in the adhesive agent 41 is 10 vol %, the electric charge density measured was about 3.9 nC/m$^2$. In contrast, it can be confirmed that the electric charge density measured was slightly over 1.0 nC/m$^2$ if the volumetric fraction of the piezoelectric material is 0 vol %, namely if no piezoelectric material is mixed with the adhesive agent.

As noted above, if the piezoelectric material is added to the adhesive agent in a predetermined volume, the electric charge density is far greater than that of the adhesive agent with which no piezoelectric material is mixed. Particularly, in the case that the piezoelectric material 43 is mixed with the adhesive agent 41 by a volumetric fraction of 5 vol % to 10 vol %, the electric charge density measured is in the range of 3.9 nC/m$^2$ 4.3 nC/m$^2$, which is greater than the electric charge density available in other range of volumetric fractions.

More specifically, referring to FIG. 7, it can be confirmed that the bonding target objects 44 and 45 bonded by the adhesive agent 41 containing quartz particles as the piezoelectric material 43 have a greater fatigue life than the bonding target objects bonded by the adhesive agent containing no quartz particle. Particularly, in the event that the piezoelectric material 43 is mixed with the adhesive agent 41 by a volumetric fraction of about 5 vol % to about 10 vol %, the fatigue life becomes greater than the fatigue life available in other range of volumetric fractions.

The volumetric fraction of the piezoelectric material 43 in the adhesive agent 41 may vary with environmental parameters but is preferably in the range of about 5 vol % to about 30 vol %. In certain embodiments, the volumetric fraction of the piezoelectric material is about 3%, about 4%, about 5%, about 5.5%, about 6%, about 6.5%, about 7%, about 8%, about 9%, about 10%, about 11%, about 12%, about 14%, about 16%, about 18%, about 20%, about 22%, about 25%, about 28%, about 30% or about 35%. In some embodiments, the volumetric fraction of the piezoelectric material may be within a range defined by two of the foregoing volumetric fractions of the piezoelectric material. It is preferred that the electrically conductive material 11, 21 or 31 has a volumetric fraction in the range of about 5 vol % to about 30 vol %. In certain embodiments, the volumetric fraction of the conductive material is about 3%, about 4%, about 5%, about 5.5%, about 6%, about 6.5%, about 7%, about 8%, about 9%, about 10%, about 11%, about 12%, about 14%, about 16%, about 18%, about 20%, about 22%, about 25%, about 28%, about 30% or about 35%. In some embodiments, the volumetric fraction of the conductive material may be within a range defined by two of the foregoing volumetric fractions of the piezoelectric material.

Figure 8:
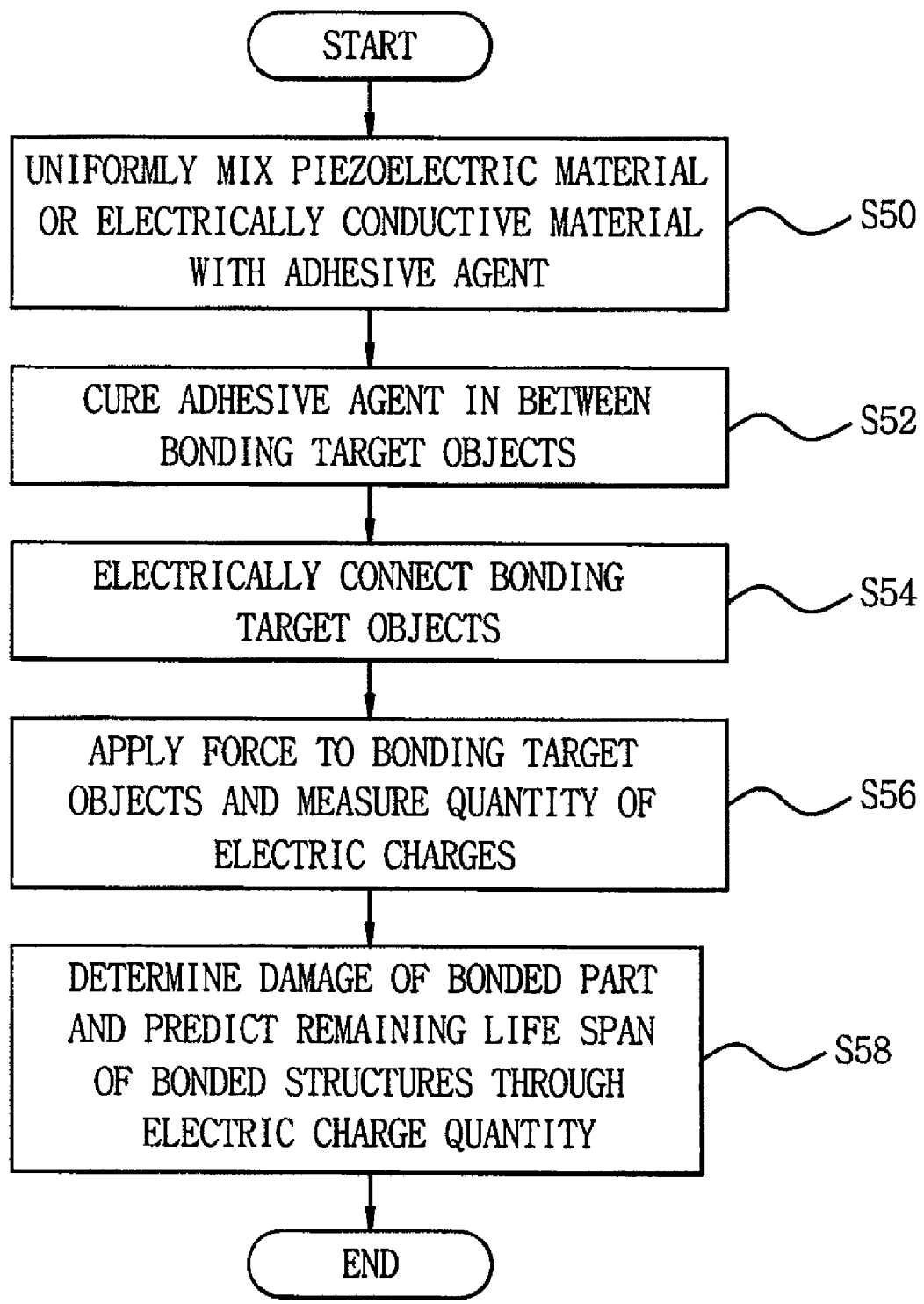
FIG. 8 is a flowchart illustrating to a method for testing bonded part integrity of bonded structures in accordance with an embodiment of the present invention.

FIG. 8 is a flowchart illustrating to a method for testing bonded part integrity of bonded structures in accordance with an embodiment of the present invention. In order to test the bonded part integrity, initially, the piezoelectric material or the electrically conductive material is uniformly mixed with the adhesive agent (S50). In this regard, the piezoelectric material 13 or 23 is comprised of a material having the predetermined shape the piezoelectric characteristic as described above. The electrically conductive material 33 may be a powder having electric conductivity.

A variety of means may be employed to uniformly mix the piezoelectric material 13 or 23 or the electrically conductive material 33 with the adhesive agent 11, 21 or 31. Specifically, the adhesive agent 11, 21 or 31 and the piezoelectric material 13 or 23 or the electrically conductive material 33 are jointly put into and mixed by a mechanical mixer. Alternatively, the piezoelectric material 13 or 23 or the electrically conductive material 33 may be mixed with the adhesive agent 11, 21 or 31 through the use of an ultrasonic vibration generated by an ultrasound generator.

Just after the piezoelectric material 13 or 23 or the electrically conductive material 33 has been uniformly mixed with the adhesive agent 11, 21 or 31, the adhesive agent 11, 21 or 31 thus obtained is allowed to cure in between the bonding target objects 14, 24 or 34 (S52). For this purpose, the adhesive agent 11, 21 or 31 is applied between the bonding target objects 14, 24 or 34 and then subjected to heating. Thereafter, the bonding target objects 14, 24 or 34 are cooled down while being pressed against one another with the bonding target objects 14, 24 or 34 interposed therebetween. As a result, the adhesive agent 11, 21 or 31 is fixedly secured to between the bonding target objects 14, 24 or 34. After the adhesive agent 11, 21 or 31 has been cured, an electric current is caused to flow through adhesive agent 11, 21 or 31 while heating the latter, thereby aligning the electric field direction of the piezoelectric material 13 or 23 or the electrically conductive material 33. Such an aligning process is referred to as "polarization" wherein the electric current is supplied such that the piezoelectric material 13 or 23 or the electrically conductive material 33 can be oriented along the direction in which a force is applied in the test process.

Once the adhesive agent 11, 21 or 31 has been cured in and fixedly secured to between the bonding target objects 14, 24 or 34, one of the bonding target objects 14, 24 or 34 is electrically connected to the other (S54). Conductive wires 16, 26 or 36 are used in making electrical connection between the bonding target objects 14, 24 or 34, in which case the conductive wires 16, 26 or 36 are respectively associated with the terminals of an electric charge quantity measuring device 18, 28 or 38.

After the ends of the bonding target objects 14, 24 or 34 have been connected to the terminals of the electric charge quantity measuring device 18, 28 or 38, a force is applied to the bonding target objects 14, 24 or 34 and the quantity of electric charges flowing therebetween is measured (S56). If the force is exerted on the bonding target objects 14, 24 or 34, the adhesive agent 11, 21 or 31 emits electric charges by itself owing to the piezoelectric characteristic thereof. Particularly, since the adhesive agent 11, 21 or 31 is produced by admixing the piezoelectric material 13 or 23 or the electrically conductive material 33, it can transmit electrical signals with improved sensitivity. As a result, when a force is applied to the bonding target objects 14, 24 or 34, it is possible to measure the quantity of electric charges flowing through the conductive wires 16, 26 or 36 between the bonding target objects 14, 24 or 34.

Different kinds of forces are exerted to the bonding target objects 14, 24 or 34 depending on the application of bonded structures. In other words, a compression stress or a sheer stress may be applied for example. In the case where the sheer stress is exerted, it is preferred that piezoelectric monofilaments are mixed with the adhesive agent.

After the quantity of electric charges has been measured, existence of bonding damage between the bonding target objects and the adhesive agent is determined based on the quantity of electric charges, and the remaining life span of the bonded structures is predicted based on a data indicating a correlation between the quantity of electric charges and a predetermined fatigue life (S58). If the bonding condition is bad between the bonding target objects 14, 24 or 34 and the adhesive agent 11, 21 or 31, namely if the bonding surface is reduced, the effective bonding cross-sectional area for supporting a load is also subject to reduction. Such reduction in the effective cross-sectional area makes greater the stress developed, thus ensuring that an increased quantity of electric charges is detected as compared to the case where the bonding condition remains good. The increased quantity of electric charges means deterioration in the bonding condition of the bonded structure.

Figure 1:
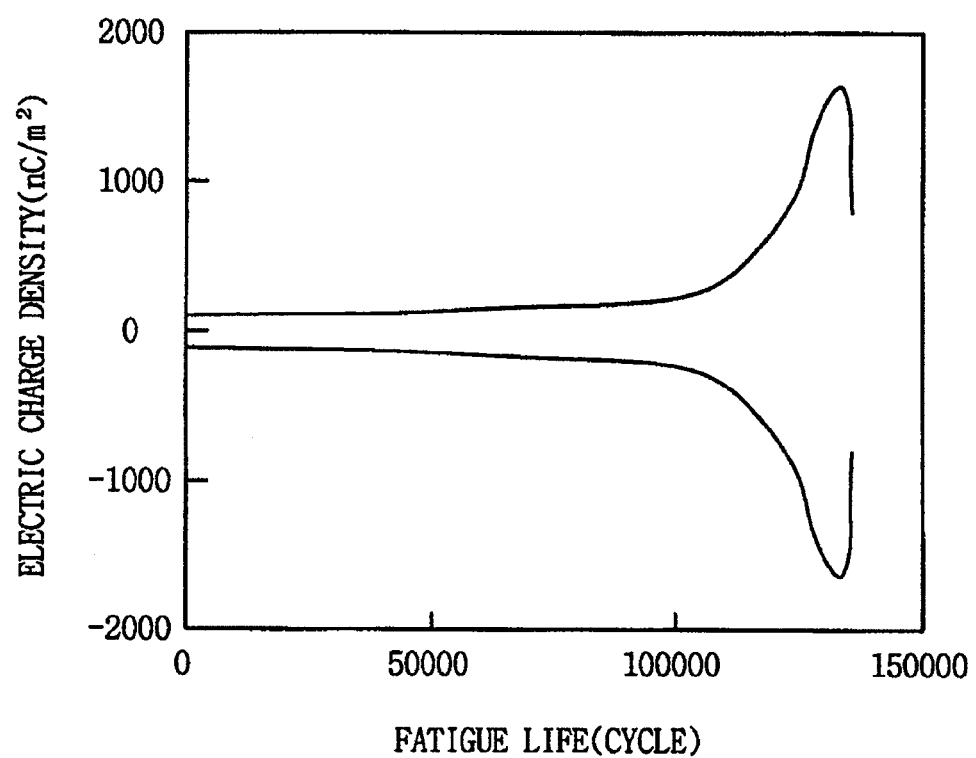
FIG. 1 is a graph representing the correlation between an electric charge density and a fatigue life at the time when an adhesive agent receives a specific fatigue load.

With a view to predict the remaining life span of the bonded structures, the correlation between an electric charge density and a fatigue life measured in advance for a predetermined stress is stored as a data table as illustrated in FIG. 1. Therefore, in the event that a force is applied to the bonding target objects 14, 24 or 34 at a specific time, the electric charge density can be calculated based on the quantity of electric charges measured, and the fatigue life under the electric charge density thus measured can be predicted through the data arranged in advance.

The structure discussed in the above embodiments may be used in an airplane. The structure in the above embodiments may be used in a ship, for example, a ship having a LNG tank.

As described in the foregoing, embodiments of the present invention makes it possible to test bonded part integrity of adhesively bonded structures with enhanced sensitivity by admixing an adhesive agent with a piezoelectric material or a conductive material. Further, embodiments of the present invention require no separate signal amplifier because an increased quantity of electric charges is generated. In addition, embodiments of the present invention makes use of an adhesive agent admixed with a piezoelectric material or a conductive material whose thermal expansion coefficient is relatively small. This reduces the residual stresses and increases the strength, thus proving a beneficial effect of enhancing the fatigue property of adhesively bonded structures.

As described above, this application is a continuation-in-part application under 35 U.S.C. § 365(c) of International Application No. PCT/KR2005/000543 (the international application). However, claims 1-14 and 17-22 are supported by the original specification of the international application, and therefore, are entitled to at least the filing date of the international application.

Although certain embodiments of the present invention have been described for illustrative purposes, it should be noted that the invention is not limited to the particular embodiments disclosed herein. It will be apparent to those skilled in the art that various changes or modifications may be made thereto within the scope of the invention defined by the appended claims.

What is claimed is:

1. An apparatus comprising:
a first piece comprising a first surface;
a second piece comprising a second surface facing the first surface;
an adhesive layer interposed between the first and second surfaces, wherein the adhesive layer contacting and integrating the first and second surfaces;
wherein the adhesive layer comprises an adhesive material with a piezoelectricity and piezoelectric particles dispersed in the adhesive material, wherein the piezoelectric particles have substantially higher piezoelectricity than the adhesive material.

2. The apparatus of claim 1, wherein the adhesive layer is configured to generate electric charges upon application of sufficient force between the first and second pieces.

3. The apparatus of claim 1, wherein the adhesive material comprises an epoxy polymer resin.

4. The apparatus of claim 1, wherein the piezoelectric particles comprise at least one selected from the group consisting of piezoelectric crystal particles, piezoelectric ceramic particles, piezoelectric polymer particles and piezoelectric semiconductor particles.

5. The apparatus of claim 1, wherein the piezoelectric particles comprise at least one selected from the group consisting of PZT(Pb(Zn—Ti)O$_3$, PVDF, PVC, nylon, rubber and quartz.

6. The apparatus of claim 1, wherein the adhesive material has a piezoelectric stress constant smaller than about 0.1 pC/N.

7. The apparatus of claim 1, wherein the piezoelectric particles have a piezoelectric stress constant greater than about 1 pC/N.

8. The apparatus of claim 1, wherein the piezoelectric particles have a piezoelectric stress constant greater than about 30 pC/N.

9. The apparatus of claim 1, wherein the total volume of the piezoelectric particles is from about 5% to about 30% of the volume of the adhesive layer.

10. The apparatus of claim 1, wherein at least part of the piezoelectric particles has a particle size from about 10 nm to about 10 µm.

11. The apparatus of claim 1, further comprising:
a first electrode as part of the first piece or as separate and interposed between the first piece and the adhesive layer;
a second electrode as part of the second piece or as separate and interposed between the second piece and the adhesive layer; and
wherein the adhesive layer is configured to generate electric charges upon application of sufficient force between the first and second pieces.

12. The apparatus of claim 1, wherein at least part of the piezoelectric particles have an elongated shape elongated in a longitudinal direction thereof, wherein the longitudinal direction is oriented generally perpendicular to the first surface.

13. The apparatus of claim 1, wherein at least part of the piezoelectric particles have an elongated shape elongated in a longitudinal direction thereof, wherein the longitudinal direction is oriented generally parallel to the first surface.

14. The apparatus of claim 1, wherein at least one of the first and second pieces receives a substantially constant pressure which applies a force in a direction, wherein the direction comprises at least one of a first directional component perpendicular to the first surface and a second directional component perpendicular to the first component.

15. The apparatus of claim 1, wherein the apparatus comprises an airplane.

16. The apparatus of claim 1, wherein the apparatus comprises a ship comprising a tank for containing liquefied gas.

17. A method of testing bonded pieces, comprising:
providing the apparatus of claim 1;
applying a predetermined amount of pressure onto at least one of the first and second pieces so as to apply a force to the adhesive layer, whereby the adhesive layer generates electric charges in the adhesive layer;
detecting a charge density of the electric charges; and
processing the charge density.

18. The method of claim 17, wherein processing the charge density is to determine the stability of the interconnection of the first and second pieces via the adhesive layer.

19. The method of claim 17, wherein processing comprises comparing the charge density with a reference value.

20. The method of claim 19, wherein the reference value comprises a charge density detected from the adhesive layer at a prior time using the same amount of force applied onto at least one of the first and second pieces in the same or substantially the same manner.

21. The method of claim 17, wherein processing the charge density is to estimate life expectancy of the interconnection of the first and second pieces via the adhesive layer.

22. The method of claim 17, wherein processing the charge density is to determine an existence of damage to the adhesive layer.

* * * * *